United States Patent
Hodosh

(10) Patent No.: US 7,125,543 B2
(45) Date of Patent: Oct. 24, 2006

(54) METHOD AND COMPOSITION FOR PREVENTING TOOTH HYPERSENSITIVITY WHEN USING PASSIVE BLEACHING AGENTS

(76) Inventor: Milton Hodosh, 243 Elmwood Ave., Providence, RI (US) 02907

( * ) Notice: Subject to any disclaimer, the term of this patent is extended or adjusted under 35 U.S.C. 154(b) by 0 days.

(21) Appl. No.: 11/230,404

(22) Filed: Sep. 20, 2005

(65) Prior Publication Data

US 2006/0013778 A1    Jan. 19, 2006

Related U.S. Application Data

(63) Continuation of application No. 09/072,504, filed on May 4, 1998, now abandoned.

(51) Int. Cl.
*A61K 8/20* (2006.01)
*A61K 8/22* (2006.01)

(52) U.S. Cl. ............... 424/53; 424/51; 424/52; 433/215; 433/216; 433/217.1

(58) Field of Classification Search ............ None
See application file for complete search history.

(56) References Cited

U.S. PATENT DOCUMENTS

| 5,486,350 | A | * | 1/1996 | Norfleet et al. | 424/49 |
| 5,928,628 | A | * | 7/1999 | Pellico | 424/49 |
| 6,306,370 | B1 | * | 10/2001 | Jensen et al. | 424/49 |
| 6,419,905 | B1 | * | 7/2002 | Alvarez Hernandez | 424/53 |

* cited by examiner

*Primary Examiner*—Frederick Krass
(74) *Attorney, Agent, or Firm*—Salter & Michaelson

(57) ABSTRACT

Dental bleaching compositions, for example in the form of liquids, gels, creams, pastes and ointments, comprising a peroxide releasing compound and from 1% to 35% by weight of a potassium-containing compound such as potassium nitrate, wherein the potassium nitrate is present in a safe and effective amount to prevent tooth hypersensitivity in the patient during the bleaching process. The potassium nitrate contemplated by the invention is compatible with peroxide yielding bleaching compounds such as peroxide, carbamide peroxide, calcium peroxide, zinc peroxide, magnesium peroxide and sodium perborate. Potassium nitrate is complimentary and synergistic with the peroxide bleaching agents contemplated by the invention and enhances the release of oxygen to the tooth enamel. Also contemplated are methods of bleaching teeth comprising application of the dental bleaching compositions of the invention.

16 Claims, No Drawings

METHOD AND COMPOSITION FOR PREVENTING TOOTH HYPERSENSITIVITY WHEN USING PASSIVE BLEACHING AGENTS

This application is a continuation of U.S. Ser. No. 09/072,504 filed on May 4, 1998, now abandoned.

FIELD OF THE INVENTION

This invention is in the field of compositions and methods of treatment for dental bleaching agents, and more specifically in the prevention of post-bleaching induced hypersensitivity.

BACKGROUND OF THE INVENTION

The process of dental bleaching is an increasingly popular practice in dentistry to combat the problem of staining or discoloration of teeth.

The enamel layer of teeth is composed of hydroxyapatite. It is believed that the porous nature of the enamel is attributed to the crystalline structure of hydroxyapatite, which allows staining agents and discoloring substances to permeate the enamel, thereby discoloring teeth. Substances that come in contact daily with teeth and that can stain or reduce the "whiteness" of teeth include foods, tobacco products, tea, coffee, betel nut, plants and food products. These substances permeate the enamel of the teeth and with continued contact impart noticeable discoloration to the teeth.

In addition, teeth may become stained from excessive intake of fluoride (endemic fluorosis). In young persons, the administration of tetracycline during tooth formation may cause staining. Generalized intrinsic staining can result from systemic conditions and diseases such as cystic fibrosis, congenital hematoporphia and dentinogenesis imperfecta.

Since white or unstained teeth are considered to improve a person's appearance, it is generally desired by patients to try to increase the whiteness of the teeth. Methods of improving the whiteness of teeth include bleaching methods which can be used to ameliorate the staining of teeth. However, known effective bleaching procedures for teeth also result in the undesired effect of tending to produce hypersensitivity or supersensitivity of the teeth. It has been reported that 74% of incidents of dental bleaching result in post-bleaching pain (hypersensitivity) to the patient. Bleaching compositions generally use peroxide or peroxide yielding compounds which have tended to involve the activation of peroxide by light sources such as photo flood light, ultraviolet light, or by heat methods such as convection heat or by the application of heat directly to teeth. These methods require the use of high concentrations of peroxide, such as in the form of Superoxol® or a 35% peroxide composition, which not only cause hypersensitivity but also have the potential to damage oral and facial tissues.

Passive bleaching involves the use of bleaching agents supplied directly in dentifrice compositions for brushing the teeth, or gels, foams, creams or pastes which are applied in prefabricated trays and/or in custom trays fabricated with reservoirs to hold bleaching preparations in extended intimate contact with the teeth for longer periods of time. Passive bleaching agents have been used with photo flood lights and with lasers. It is now understood that the teeth can be made whiter by passive bleaching methods using peroxide releasing compounds such as carbamide peroxide, also known as urea peroxide, usually in the amount of 10% to 20% by weight of the composition. The higher concentrations of the peroxide yielding compounds are used to effect faster and more effective bleaching (power bleaching). Other peroxide releasing compounds that have been known in the prior art include sodium perborate, zinc peroxide, calcium peroxide and magnesium peroxide, and other compounds which can release peroxide effectively with bubbling oxidizing force.

In general, higher concentrations of peroxide yielding compounds improve the efficacious bleaching capabilities of the composition. However, the higher peroxide concentrations exacerbate the sequelae of hypersensitivity or supersensitivity. The pain resulting from hypersensitivity or supersensitivity is considered to be a warning that the tooth and pulpal tissues have experienced a severe insult. Faster and more aggressive bleaching techniques, such as with the use of higher concentrations of peroxide yielding compounds, results in more severe and higher incidence of post-bleaching hypersensitivity to thermal, chemical and tactile stimuli.

Dental bleaching compositions are described in a number of references, including U.S. Pat. Nos. 5,098,303; 5,234,342; 5,376,006; and 5,409,63 1, all to Fischer, which are hereby incorporated by reference. The Fisher patents describe tooth bleaching dental gel composition comprising carbamide peroxide, water, glycerin, carboxypolymethylene (Carbopol) and sodium hydroxide. Dental bleaching compositions are also described in U.S. Pat. No. 5,631,000, to Pellico et al., which is hereby incorporated by reference.

The use of potassium nitrate as a compound for desensitizing teeth is disclosed in U.S. Pat. No. 3,863,006, which is hereby incorporated by reference. Potassium nitrate has also been disclosed as useful for treatment of canker sores in U.S. Pat. No. 4,191,750, hereby incorporated by reference; useful for preserving dental pulp, in U.S. Pat. No. 4,343,608, hereby incorporated by reference; useful for treating gingival and periodontal tissues, in U.S. Pat. No. 4,400,373, hereby incorporated by reference; and useful for treating post-restoration dental pain, in U.S. Pat. No. 5,153,006, hereby incorporated by reference.

Other patents, including for example U.S. Pat. Nos. 5,256,402 and 5,648,399, have described the use of potassium nitrate in dentifrice compositions as a treatment for hypersensitivity. However, the use of potassium nitrate incorporated into dental tray bleaching compositions has not been previously described as being capable of preventing tooth hypersensitivity.

Another patent, U.S. Pat. No. 5,522,726 has described the use of a composition having a high concentration of potassium, such as potassium nitrate, for anesthetizing teeth requiring preparation, caries removal or manual manipulation thereof.

SUMMARY OF THE INVENTION

It has now been surprisingly discovered that the use of 1% to 35% of a potassium-containing composition, such as potassium nitrate, by weight in passive bleaching materials comprising a peroxide releasing material prevents the frequently seen (up to 75% of the time) tooth hypersensitivity from occurring. The potassium nitrate contemplated by the invention is uniquely compatible with peroxide yielding bleaching compounds such as peroxide, carbamide peroxide, calcium peroxide, zinc peroxide, magnesium peroxide and sodium perborate.

In another aspect of the invention, it has also been found that the potassium-containing composition, specifically potassium nitrate, which is known to be an oxidizing agent, is complimentary and synergistic with the peroxide bleaching agents contemplated by the invention and actually enhances the release of oxygen to the tooth enamel.

Preferred compositions of the invention may include from 1% to 35% by weight of potassium nitrate. In more preferred compositions of the invention, the potassium nitrate is present in the amount of 1–20%. In even more preferred embodiments, potassium nitrate is present in the amount of 1–8%. In a most preferred embodiment, potassium nitrate is present in a composition in the amount of about 5% by weight. The invention contemplates the use of higher amounts of potassium nitrate with higher amounts of peroxide releasing compounds.

The invention also contemplates the use of a potassium-containing composition comprising a compound other than potassium nitrate such as potassium bicarbonate, potassium biphthalate, potassium bromide, potassium chromate, potassium dichromate, potassium phosphate, potassium sulfate, potassium chromium sulfate, potassium thiocyanate, potassium alum, potassium bitartrate, potassium bromate, potassium carbonate, potassium chlorate, potassium chloroplatinate, potassium hydroxide, potassium perchlorate, potassium persulfate, potassium oxalate, potassium azide, potassium flouride, potassium hydrogen sulfate, potassium iodate, potassium chloride, potassium acetate or potassium tartrate. For the purposes of the invention and the description herein, these potassium-containing compounds may be used instead of potassium nitrate.

The invention contemplates the use of the potassium-containing compound such as potassium nitrate in liquids, gels, creams, pastes, foams and ointments with tooth bleaching compositions for the prevention of tooth hypersensitivity from occurring. In an additional embodiment, the invention is in the form of a lacquer or varnish or other surface coating that is painted to the teeth, thereby providing a longer contact/coating period. In all embodiments of the invention, the use of the potassium-containing compound such as potassium nitrate is a unique one-step method of preventing hypersensitivity when combined with the bleaching compositions known in the art, and is different from known methods of using potassium-containing compounds potassium nitrate for the treatment of hypersensitivity that has already occurred. This is an improvement over the known use methods of this technology, and the invention is directed to a method of preventing the usual tooth hypersensitivity from occurring following the application of the dental bleaching composition of the invention to teeth.

DETAILED DESCRIPTION OF THE INVENTION

By "orally compatible" is meant compositions and ingredients which are generally regarded as safe for use in the oral cavity.

By "oral compositions" is meant a product which in the ordinary course of its use is retained in the oral cavity for a time sufficient to contact substantially all of the dental surfaces and/or oral tissues for purposes of oral activity.

By "safe and effective amount" is meant a sufficient amount of material to provide the desired benefit while being safe to the hard and soft tissues of the oral cavity.

By "carrier" is meant a suitable vehicle which is orally compatible and can be used to apply the present compositions in the oral cavity.

It is to be noted that the composition of the invention is a dental bleaching composition, and can be distinguished from dentrifices. A "dentrifice" is a substance, such as a liquid, paste, gel or powder, used with a toothbrush or similar instrument for the purpose of cleaning the accessible parts of teeth. Dentrifices generally contain a fluoride releasing compound and an abrasive.

The bleaching composition of the invention may take the form of liquids, gels, pastes, creams, ointments or foams. In each of these forms, the bleaching composition of the invention includes a peroxide releasing compound, such as carbamide peroxide (Peroxomer®), and potassium nitrate in the amount of from 1% to 35% by weight. Other potassium-containing compounds instead of potassium nitrate, such as those listed above, may be used instead of potassium nitrate in the bleaching composition.

The bleaching compositions of the present invention can also include ancillary ingredients such as orally compatible carriers or matrices, to provide commercially acceptable products. The carrier for the dental bleaching compositions of the invention include water. The water used in the compositions of the invention is preferably deionized and free of impurities. Water may comprise up to about 50%, preferably from about 20% to about 40%, by weight of the dental bleaching composition herein.

The composition of the invention may also include glycerin, which acts as a humectant and flavoring agent, or sorbitol, aloes such as aloe vera, polyethylene glycols, propylene glycols, polyols or polypropylene. Flavoring agents which may be included in the composition of the invention include mint flavorings, oil of wintergreen, oil of peppermint, oil of spearmint, oil of sassafras, and oil of clove. Sweetening agents may also be used, and include xylitol, aspartame, acesulfame, saccharin, dextrose, levulose and sodium cyclamate. Flavoring and sweetening agents are generally included in the dental bleaching compositions of the invention in the amount of from about 0.005% to about 2% by weight. Combinations of one or more humectants, flavoring agents or sweetening agents is also contemplated by the invention.

The composition of the invention may comprise a high viscosity matrix material, such as carboxypolymethylene (Carbopol).

A water soluble cellulosic ether, such as hydroxyalkyl celluloses such as hydroxypropyl cellulose, hydroxypropyl ethylcellulose, or hydroxypropyl methylcellulose, or carboxymethyl cellulose, may also be included in the dental bleaching composition. Further, the composition may comprise a base, such as sodium hydroxide.

The composition may also comprise orally compatible preservatives of the type commonly used in dental compositions, such as sodium benzoate.

The composition may also comprise orally compatible coloring agents or colorants of the type commonly used in dental compositions.

In the form of a gel, glycerin may be present in the amount up to about 64% by weight; proplyene glycol may be present in the amount of up to about 55% by weight; polyethylene glycol may be present in the amount of up to about 50% by weight; deionized water may be present in the amount of up to about 50% by weight; carboxypolymethylene may be present in the amount of up to about 12% by weight; hydroxyalkyl cellulose may be present in the amount of up to about 15% by weight; carbamide peroxide may be present in the amount of about up to about 30% by weight; and potassium nitrate may be present in the amount of about 1% by weight to 35% by weight. Other potassium-containing compounds instead of potassium nitrate, such as those listed above, may be used instead of potassium nitrate in the gel.

The composition of the invention in its liquid form, such as in the form of a solution, includes an orally compatible solvent, such that the solvent may come into contact with the dental and gingival tissues of a person. Suitable solvents include water and water-immiscible solvents, such as ethanol, isopropyl alcohol, propylene glycol, polyethylene glycol, glycerol, methylcellulose, cellulose, esters, morpholines, dioxane, dimethylsulphoxide and the like. The composition of the invention in the form of a liquid may also comprise a stabilizer, such as calcium disodium edetate, deforoxamine mesylate or tetrasodium edetate.

In its embodiment as a foam, the composition of the invention may include any of the various types of emulsifying agents or surfactants commonly used in dental compositions. Exemplary emulsifying agents are those which are reasonably stable and foam throughout a wide pH range, including non-soap anionic, nonionic, cationic, zwitterionic and amphoteric organic synthetic detergents.

In addition to the higher fatty acid soaps, other synthetic anionic organic detergents may be used as replacements or partial replacements. Among the useful anionic detergents are the higher alkyl sulfates, higher alkyl sulfonates, higher alkyl benzene sulfonates, ethoxylated higher fatty alcohol sulfates, monoglyceride sulfates, higher fatty acid amides of amino-lower carboxylic acids, such as sodium lauroyl sarcoside, phosphates and phosphonates corresponding to the above mentioned sulfates and sulfonates, and sulfates and sulfonates of the well-known nonionic surface active agents, such as those of polyoxyethylene glycols, of block copolymers of ethylene oxide and propylene oxide, chain terminated with propylene glycol and of polyethoxylated middle alkyl phenols. Specific examples of useful anionic synthetic organic detergents or surface active agents for inclusion in this formula are: triethanolamine lauryl sulfate; linear dodecyl benzene sodium sulfonate; potassium coconut oil monoglyceride sulfate; ammonium paraffin sulfonate; and ammonium paraffin sulfonate and ammonium polyoxyethylene stearyl alcohol sulfate.

The foam composition of the invention may also include a foam stabilizer or mixture of such stabilizers. Such materials may include organic gums and colloids, serving as thickening agents to maintain the foam in the shape in which it was applied, but it will often be found preferable to utilize the lower alkanolamides of higher fatty acids for this purpose. An exemplary foam stabilizer is lauric-myristic diethanolamide, or LMDEA.

In its various embodiments, the composition of the invention may be within a range of pH's which are safe for the hard and soft tissue of the mouth. Such pH's are generally from about 3 to about 10, preferably from about 4 to about 8.

The dental bleaching composition of the invention is designed for application to teeth by methods commonly used in the art. For example, the composition may be disposed in a applicator tray which is insertable into the mouth as a mouthpiece surrounding respectively the upper and lower teeth and adjacent periodontal tissue. Such trays are commonly rigid and made of the vinyl plastic material and are in the form of an arcuate U-shaped mouth piece. Applicator trays are described in U.S. Pat. No. 5,575,654, to Fontenot, which is hereby incorporated by reference.

EXAMPLES

The following Examples illustrate various exemplary formulations of the compositions of the invention in the form of gels.

TABLE I

| | Example | | |
| --- | --- | --- | --- |
| | 1 | 2 | 3 |
| Carbamide peroxide | 10% | 20% | 14% |
| Water (deionized) | 21% | 20% | 10% |
| Potassium Nitrate | 5% | 7% | 6% |
| Glycerin | 52% | 33% | 64% |
| Hydroxyalkyl Cellulose | 7% | 12% | 3.5% |
| Sodium Hydroxide | 5% | 8% | 2.5% |

Set forth in Table I above are three examples of formulations of the invention in the form of gels. It is noted that Example 2, with the highest concentration of carbamide peroxide, has similarly higher percentages of potassium nitrate for best effects. For maximum results a dental tray holds these preparations adjacent to discolored tooth surfaces.

The use of hydroxyalkyl cellulose results in bleaching compositions of high viscosity. As a result, the dilution of compositions by saliva is difficult, and the composition stays within the tray longer providing a sustained relief of the effect of the peroxide releasing properties of the carbamide peroxide to the patient's teeth.

A fourth example of the composition of the invention in the form of a gel is set forth below at Table II with its components in weight percent.

TABLE II

| Example 4 | |
| --- | --- |
| Water (deionized) | 6% |
| Propylene Glycol | 32% |
| Glycerin | 38% |
| Xylitol | 9% |
| Peroxomer ® 407 | 7% |
| Potassium Nitrate | 3% |
| *Aloe Vera* | 3% |
| Mint or other flavoring | 2% |

Example 4 is used preferably with a dual chamber dental tray as hydrogen peroxide is stable at lower pH's but is effective at higher pH's. The dual chamber tray contains an activator and mixes the compositions together.

A fifth example of the composition of the invention in the form of a gel is set forth below in Table III with its components in weight percents.

TABLE III

| Example 5 | |
| --- | --- |
| Carbamide Peroxide | 17% |
| Water (deionized) | 2% |
| Hydroxyethyl cellulose | 14% |
| Potassium nitrate | 33% |
| Carbopol | 30% |
| Flavoring agents | 2% |
| Coloring agents | 2% |

The compositions of the invention may be formed by any of the methods commonly used in the art, such as by adding and admixing the ingredients in a suitable vessel, for example a stainless steel tank. Mixers may be used to mix the ingredients to form a homogeneous dispersion such as a gel. The components that are mixed together are added in amounts to produce a resulting composition with the weight percents disclosed in this specification, for example in the above Examples 1 to 5.

It is understood that upon prolonged storage or upon use, such as upon disposal into dental trays or upon contact with a patient's teeth, the compositions of the invention may undergo chemical or physical reactions so that the chemical nature of the components are changed. For example, as described above the carbamide peroxide or other peroxide releasing compound decomposes over time so that peroxide is released. Further, the humectants such as propylene glycol, may absorb water to form new compounds. It is understood that these chemical and physical reactions may change the weight percents of the composition that are present at formation.

While there have been described particular embodiments of the invention, those skilled in the art will realize that changes and modifications can be made thereto without departing from the spirit of the invention and it is intended to claim all such changes and modifications that fall within the true scope of the invention.

Having thus described the invention, what is claimed is:

1. A dental bleaching gel for inhibiting tooth hypersensitivity in a patient undergoing dental bleaching, comprising a combination of 5–30% by weight of a peroxide releasing tooth bleaching compound and from 1% to 35% by weight of potassium-containing compound, based on the total weight of the composition, wherein said potassium-containing compound is present in a safe and effective amount to inhibit tooth hypersensitivity from occurring upon application of the tooth bleaching composition to teeth, said composition not being a dentifrice and not containing an abrasive and wherein said potassium containing compound is selected from the group consisting of potassium bicarbonate, potassium biphthalate, potassium bromide, potassium chromate, potassium dichromate potassium phosphate, potassium sulfate, potassium chromium sulfate, potassium thiocyanate, potassium alum, potassium bitartrate, potassium bromate, potassium carbonate, potassium chlorate, potassium chloroplatinate, potassium perchlorate, potassium persulfate, potassium oxalate, potassium azide, potassium hydrogen sulfate, potassium iodate, potassium chloride, potassium acetate and potassium tartrate.

2. The dental bleaching gel of claim 1, wherein said peroxide releasing compound is selected from the group consisting of carbamide peroxide, sodium perborate, zinc peroxide, calcium peroxide, and magnesium peroxide, and mixtures thereof.

3. The dental bleaching gel of claim 1, wherein said potassium containing compound is present in the amount of from 1%–20% by weight, based on the total weight of the composition.

4. The dental bleaching gel of claim 1, wherein said potassium containing compound is present in the amount of from 1%–8% by weight, the total weight of the composition.

5. The dental bleaching gel of claim 1, wherein said potassium containing compound is present in the amount of from 5% by weight, based on the total weight of the composition.

6. An orally compatible dental bleaching gel comprising
(a) from 10 to 20% by weight carbamide peroxide, based on the total weight of the composition;
(b) from 10 to 25% by weight deionized water, based on the total weight of the composition;
(c) from 5 to 7% by weight a potassium-containing compound, based on the total weight of the composition; and
(d) from 30 to 65% by weight glycerin, based on the total weight of the composition, said dental bleaching gel not being a dentifrice and not containing an abrasive and wherein said potassium-containing compound is selected from the group consisting of potassium bicarbonate, potassium biphthalate, potassium bromide potassium chromate, potassium dichromate, potassium phosphate, potassium sulfate, potassium chromium sulfate, potassium thiocyanate, potassium alum, potassium bitartrate, potassium bromate, potassium carbonate, potassium chlorate, potassium chloroplatinate, potassium perchlorate, potassium persulfate, potassium oxalate, potassium azide, potassium hydrogen sulfate, potassium iodate, potassium chloride, potassium acetate and potassium tartrate.

7. The gel of claim 6, further comprising sodium hydroxide.

8. The gel of claim 6, further comprising a matrix material.

9. The gel of claim 8, wherein said matrix material is carboxypolymethylene.

10. The gel of claim 7, further comprising hydroxyalkyl cellulose.

11. The gel of claim 6, further comprising a sweetening agent.

12. The gel of claim 6, further comprising a flavoring agent.

13. An orally compatible dental bleaching gel comprising
(a) from 5 to 10% by weight carbamide peroxide, based on the total weight of the composition;
(b) from 5 to 10% by weight deionized water, based on the total weight of the composition;
(c) from 3 to 5% by weight a potassium-containing compound, based on the total weight of the composition; and
(d) from 30 to 40% by weight glycerin, based on the total weight of the composition, and
(e) from 30 to 35% by weight propylene glycol, based on the total weight of the composition, said gel not being a dentifrice and not containing an abrasive and wherein said potassium-containing compound is selected from the group consisting of potassium bicarbonate, potassium biphthalate, potassium bromide, potassium chromate, potassium dichromate, potassium phosphate, potassium sulfate, potassium chromium sulfate, potassium thiocyanate, potassium alum, potassium bitartrate potassium bromate, potassium carbonate, potassium chlorate, potassium chloroplatinate, potassium perchlorate, potassium persulfate, potassium oxalate, potassium azide, potassium hydrogen sulfate, potassium iodate, potassium chloride, potassium acetate and potassium tartrate.

14. The gel of claim 13, further comprising a sweetening agent.

15. The gel of claim 13, further comprising a flavoring agent.

16. A method of inhibiting tooth hypersensitivity in a patient undergoing dental bleaching, comprising the step of:
applying a dental bleaching gel to the teeth comprising a combination of 5–30 percent by weight of a peroxide releasing compound and from 1% to 35% by weight a potassium-containing compound, based on the total weight of the composition wherein said potassium-containing compound is present in a safe and effective amount to prevent tooth hypersensitivity upon application of the composition to teeth, said composition not being a dentifrice and not containing an abrasive and wherein said potassium-containing compound is selected from the group consisting of potassium bicarbonate, potassium biphthalate, potassium bromide, potassium chromate potassium dichromate, potassium phosphate, potassium sulfate, potassium chromium sulfate, potassium thiocyanate, potassium alum, potassium bitartrate, potassium bromate, potassium carbonate, potassium chlorate, potassium chloroplatinate, potassium hydroxide, potassium perchlorate, potassium persulfate, potassium oxalate, potassium azide, potassium hydrogen sulfate, potassium iodate, potassium chloride, potassium acetate and potassium tartrate.

\* \* \* \* \*